United States Patent [19]

Khoï

[11] 4,006,635
[45] Feb. 8, 1977

[54] LIQUID LEVEL MEASURING PROCESS AND INDICATOR

[75] Inventor: Danny James Khoï, Saint-Cloud, France

[73] Assignee: Cermat, Courbevoie, France

[22] Filed: Nov. 6, 1974

[21] Appl. No.: 521,302

[30] Foreign Application Priority Data

Nov. 8, 1973 France ............................ 73.39672

[52] U.S. Cl. .................................. 73/302; 73/301; 73/439
[51] Int. Cl.[2] .................... G01F 23/18; G01N 9/28
[58] Field of Search ............ 73/299, 301, 302, 439

[56] References Cited

UNITED STATES PATENTS

| 1,457,406 | 6/1923 | Stancliffe | 73/302 X |
| 1,622,794 | 3/1927 | Martin | 73/301 |
| 3,023,619 | 3/1962 | Sandford | 73/302 X |
| 3,038,336 | 6/1962 | Peters | 73/301 X |
| 3,250,123 | 5/1966 | Clayton | 73/301 |
| 3,620,085 | 11/1971 | Khoi | 73/302 X |

*Primary Examiner*—Richard C. Queisser
*Assistant Examiner*—John S. Appleman
*Attorney, Agent, or Firm*—Alan H. Levine

[57] ABSTRACT

The present invention relates to a process and device for measuring the level and the specific gravity of a liquid e.g. liquified methane, contained in large-capacity tanks.

The installation comprises two hydrostatic probes for spray a neutral gas into the tank, the first probe emerging near the bottom of the tank and the second slightly below the maximum filling level, a pressure differential/electric voltage transducer each of whose two inputs is connected to a hydrostatic probe, a system for numerically displaying the level and the specific gravity of the liquid contained in the tank, at least one pick-up capable of transmitting a signal when the liquid reaches the predetermined level in the tank, and a device for adjusting the value of the specific gravity of the liquid when the liquid reaches the predetermined level in the tank.

6 Claims, 1 Drawing Figure

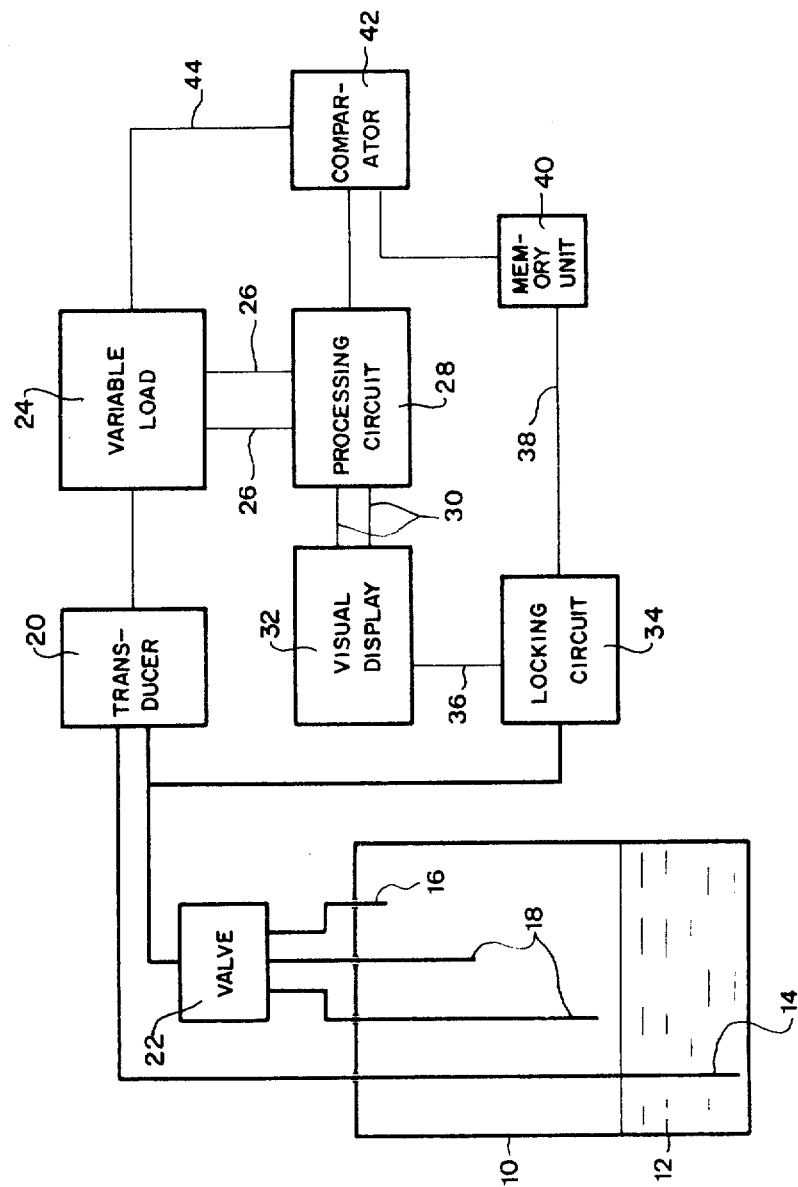

LIQUID LEVEL MEASURING PROCESS AND INDICATOR

The present invention relates to a process and a device for measuring the level and the average specific gravity of a liquid contained in large-capacity tanks, for example tanks of ships or vehicles transporting liquefied methane or other natural gas.

The measurement of liquid cargo, especially methane, has presented a particularly tricky problem since this type of product has come into existence, a problem to which no satisfactory solution has so far been found.

An object of the invention is to provide means for reasonably accurately indicating the level reached as a tank is filled — or emptied — and possibly also an indication of the specific gravity of the liquid.

According to the invention a level indicator comprises at least two hydrostatic probes opening at different levels in the tank and a transducer for giving a signal dependent on the difference between the pressures sensed by the probes, means for adjusting the value of the dependent signal and for displaying the adjusted value, and at least one pick-up for indicating when the level is at a pre-determined level in the tank.

The level of the liquid is related to the quotient of the hydrostatic pressure difference and the density or specific gravity of the liquid and if the specific gravity is only estimated an error can easily appear. However, by making the adjustment when the liquid is at the known pre-determined level it is possible to correct the estimation of the specific gravity and also the indicated level, and the corrected value of specific gravity can be stored for use while filling continues and subsequent measurements are made.

The invention includes a process of measuring the level of liquid in a tank in which a visual indication is given of the measured liquid level and when the liquid reaches a known level an adjustment is made to the indication if necessary to bring it to the known level, and the degree of adjustment is retained for giving subsequent indications.

STATEMENT OF PRIOR ART

In the past in determining the specific gravity of liquids stored in large-capacity taks, there were many factors which could falsify the results. In fact, in tanks of this type it is known to determine the level of the liquid by measuring the pressure at the head of hydrostatic probes which emerge at different levels in the liquid. These probes are supplied with a neutral spray gas after passing through the supply regulators. An installation of this type based on this measuring principle is described for example in U.S. Pat. No. 3,620,085 in the name of the applicant.

Up until now it has been generally accepted that the differential measurement of hydrostatic pressures taken at the extremity of two probes, the difference in whose depth is known, would give an exact indication of the density. In fact, the hydrostatic pressure measured at the tip of the probe is the difference in weight between the column of liquid in question and the weight of the column of neutral gas contained in the said probe. The weight of the column of neutral spray gas is not negligible in relation to the weight of the column of liquid, and also varies in relatively significant proportions as a function of both the temperature and the level of the liquid in question. Taking account of these approximations, it has proved impossible up until now to obtain very precise results concerning the level and the specific weight of a liquid contained in a tank.

The present invention avoids the disadvantages mentioned above and by making adjustments in the course of measuring makes it possible to obtain results with greater precision than 1 cm over filling heights of 35 m in addition to displaying the specific weight to four decimal places.

The invention may be carried into practice in various ways and one embodiment will now be described by way of example with reference to the accompanying drawing, of which the single FIGURE is a diagram of an arrangement for giving an indication of the level of a liquid in a tank.

The tank 10 contains a liquid 12 — liquified methane in the example being described — the level of which is to be indicated on a numerical display 32. There are a number of probes 14, 16, and 18, extending into the tank to different levels, the probe 14 opening at a level close to the bottom of the tank, the probe 16 opening at a level close to the top of the tank, and the other probes 18 opening at intermediate levels. The probes are used for spraying a neutral pressurising gas into the tank above the liquid level.

The level of the liquid is determined by measuring the hydrostatic pressure difference between the levels of the opening of the probe 14 and the opening of whichever probe is the lowest above the liquid surface, and the pressures detected by those probes are supplied as inputs to a transducer 20 arranged to produce an electrical signal output which is a measure of that difference. For that purpose a change-over valve 22 is arranged automatically to change over the connection to the low pressure input of the transducer 20 from one of the probes 18 and 16 to the adjacent probe when the level of liquid just reaches or just leaves the opening of the one probe so that it is always the probe immediately above the liquid level that is used to provide the low pressure input signal to the transducer 20.

The electrical output from the transducer 20 is fed by way of variable load 24 and lines 26 to a processing circuit 28 which provides signals representing the hydrostatic pressure difference as adjusted by the load 24 and representing the degree of adjustment in a form suitable for visual numerical display at 32. The first figure displayed is the measurement of the liquid level, and the second figure is a measurement of the liquid's specific gravity.

The load 24 conveniently comprises a rheostat whose value can be controlled by an electrical signal from a line 44 as described below. The original value will correspond with the estimated specific gravity of the liquid, since liquid level is proportional to hydrostatic pressure difference divided by liquid specific gravity.

A locking circuit 34 is triggered when the liquid level reaches a pre-determined level-conveniently the level of the opening from one of the probes 16 and 18 — to transmit a locking signal over the line 36 to lock the numerical display of the level and specific gravity on the volt meter 32. At the same time the circuit 34 triggers a memory unit 40 over a line 38 to supply a signal representing the pre-determined level as one input to a comparator 42. The other input to the comparator 42 is a signal from the circuit 28 representing the level of liquid measured. If that signal is different from the signal from the memory unit 40, a difference signal is fed over the line 44 to reset the load 24 until the measured signal at 28 does correspond with the pre-determined level. In that way the display 32 is brought into agreement with the known level, and also the new display of specific gravity will be that corresponding to the setting of the load 24 to get the correct level display, and so will be a more accurate measure of the specific gravity.

If desired each of the probes 16 and 18 can trigger the circuit 34 to set in a different pre-set level which is the level of that probe, and then there will be a number of adjustments of the load 24 during filling or emptying of the tank which will allow for some variation of the specific gravity of the liquid if it is not homogeneous.

Instead of automatically re-setting the load 24 by use of the memory unit 40 and comparator 42, it can be arranged that when the pre-set level is reached an alarm is given and the operator can manually adjust the load 24 so that the indicated level corresponds with the pre-determined level. The input to the load 24 will be locked while the adjustment is made as that obtaining when the level reaches the pre-set level. Thereafter the load setting representing the specific gravity will be recorded and memorised until there is any further re-set.

What is claimed as my invention and desire to secure by Letters Patent is:

1. An installation for continuously measuring the level and the average specific gravity of a liquid contained in a large-capacity tank, especially tanks of vessels for transporting liquefied natural gas, comprising:
    a plurality of hydrostatic probes for spraying neutral gas into the tank, the outlets of said probes being at different levels within the tank,
    a transducer having two inputs which are connectable to all of said probes but are connected at any one time to only two of said probes, said transducer converting the pressure difference between neutral gas within the two probes to which it is connected into an electric signal,
    means responsive to the electric signal from said transducer for numerically displaying the level and the specific gravity of the liquid contained in the tank,
    a variable load between said transducer and said display means for producing a signal proportional to said electric signal from said transducer, and
    a circuit responsive to the liquid level reaching the outlet of one of said probes for adjusting said variable load so that the signal provided by said variable load causes the known level of the outlet of said one probe to be displayed by said display means.

2. An installation as defined in claim 1 including at least three hydrostatic probes, the outlet of the lowermost probe opening near the bottom of the tank and the outlet of the uppermost probe opening slightly below the maximum liquid level within the tank, and a valve for connecting to said transducer the lowermost probe and the lowest one of the other probes which is above the liquid level.

3. An installation as defined in claim 1 wherein said display means includes means for producing a signal representative of the numerical display, and said responsive circuit includes means for producing a signal representative of said known level, and comparator means for receiving said two representative signals as inputs and producing an output related to the difference between said two representative signals for adjusting said variable load to cause the two representative signals to become equal.

4. An installation as defined in claim 1 wherein said responsive circuit includes a circuit for locking the numerical display of the known level on said display means when the liquid level in the tank reaches the outlet of said one probe and for maintaining that display throughout the period during which said variable load is adjusted.

5. An installation as defined in claim 1 wherein said responsive circuit responds to the liquid level reaching the outlet of each of a plurality of said probes for adjusting said variable load so that the signal provided by said variable load causes the level of the probe outlet which is at the level of the liquid to be displayed by said display means.

6. An installation as defined in claim 1 including an alarm which is activated in response to the liquid level reaching said known level.

* * * * *